(12) United States Patent
Schenker (10) Patent No.: US 8,815,601 B2
(45) Date of Patent: Aug. 26, 2014

(54) CALORIMETER AND METHOD FOR PERFORMING REACTION CALORIMETRY

(75) Inventor: Benedikt Schenker, Würenlingen (CH)

(73) Assignee: Mettler-Toledo AG, Greifensee (CH)

( * ) Notice: Subject to any disclaimer, the term of this patent is extended or adjusted under 35 U.S.C. 154(b) by 235 days.

(21) Appl. No.: 12/767,019

(22) Filed: Apr. 26, 2010

(65) Prior Publication Data

US 2010/0255588 A1 Oct. 7, 2010

Related U.S. Application Data

(63) Continuation of application No. PCT/EP2008/063364, filed on Oct. 7, 2008.

(30) Foreign Application Priority Data

Oct. 25, 2007 (EP) ...................................... 07119294

(51) Int. Cl.
| | |
|---|---|
| *G01N 25/20* | (2006.01) |
| *G01N 35/00* | (2006.01) |
| *G01K 17/04* | (2006.01) |
| *G01N 25/48* | (2006.01) |

(52) U.S. Cl.
CPC ............ *G01K 17/04* (2013.01); *G01N 25/4833* (2013.01); *G01N 25/4826* (2013.01)
USPC .................................. 436/50; 436/43; 422/51

(58) Field of Classification Search
None
See application file for complete search history.

(56) References Cited

U.S. PATENT DOCUMENTS

| | | | |
|---|---|---|---|
| 4,178,800 A | 12/1979 | Thomann | |
| 5,813,763 A * | 9/1998 | Plotnikov et al. | ............... 374/11 |
| 6,953,280 B2 * | 10/2005 | Fischer et al. | ................... 374/33 |
| 2003/0058918 A1 | 3/2003 | Fischer et al. | |
| 2005/0036536 A1 | 2/2005 | Lewis | |

FOREIGN PATENT DOCUMENTS

DE 10010291 A1 9/2001

OTHER PUBLICATIONS

Zogg, A. et al. "A New Small-Scale Reaction Calorimeter That Combines the Principles of Power Compensation and Heat Balance," Ind. Eng. Chem. Res. 2003, 42, 767-776.*
Zogg, A. et al., A New Small-Scale Reaction Calorimeter That Combines the Principles of Power Compensation and Heat Balance, Ind. Eng. Chem. Res., 2003, pp. 767-776, 42(4).

* cited by examiner

*Primary Examiner* — Yelena G. Gakh
*Assistant Examiner* — Michelle Adams
(74) *Attorney, Agent, or Firm* — Standley Law Group LLP (57) ABSTRACT

A calorimeter with at least one reactor for receiving a sample is disclosed. A reactor jacket may surround the reactor. A reactor-heating device and a reactor-cooling device serve to regulate an internal reactor temperature. The reactor-cooling device preferably comprises a thermoelectric cooling element that is thermally connected to a coolant. The reactor-cooling device and the reactor-heating device are preferably individual units, both of which are thermally connected to the reactor by way of the reactor jacket. A temperature control device is provided to control the reactor-heating device and the reactor-cooling device.

11 Claims, 4 Drawing Sheets

CALORIMETER AND METHOD FOR PERFORMING REACTION CALORIMETRY

CROSS-REFERENCE TO RELATED APPLICATIONS

This application is a continuation under 35 USC §120 of PCT/EP2008/063364, filed 7 Oct. 2008 which is, in turn, entitled to benefit of a right of priority under 35 USC §119 from European patent application 07119294.2, filed 25 Oct. 2007. The content of each of these applications is incorporated by reference as if fully recited herein.

TECHNICAL FIELD

The present invention is directed to a calorimeter, such as a reaction calorimeter. More specifically, the present invention is directed to a calorimeter, a temperature control device for use with an apparatus having a calorimeter, and a method of use thereof.

BACKGROUND

Reaction calorimeters are used, among other purposes, for the determination of chemical and/or physical parameters of a sample. The use of a fast and efficient temperature control device is important in particular for the investigation of temperature-critical samples. In temperature-critical samples it is possible that changes of the composition, structure or other chemical and/or physical properties may occur even as a result of minor temperature fluctuations. An exemplary reaction calorimeter with a temperature control device is disclosed for example in WO 02/21089 A1.

The known state of the art includes different types of reaction calorimeters. These consist in most cases of a container or reactor for the reaction medium which can be heated or cooled by an attached temperature control device. A jacket that is filled with a temperature-control liquid and envelops the reactor is frequently used for this purpose. The temperature-control liquid is connected to a heat exchanger, so that the temperature of the temperature-control liquid can be regulated.

A reaction calorimeter with a capability of recording infrared spectra is described in A. Zogg et al., Ind. Eng. Chem. Res. 2003, 42, 767-776. The reactor is in this case embedded in a metal block which consists of a metal with a good thermal conductivity. The metal block is surrounded by Peltier elements which are connected to their electrical supply source in such a way that they can heat as well as cool the metal block. To conduct away heat in a cooling mode, the Peltier elements are connected to a cryostat. The cryostat contains a coolant whose temperature is regulated depending on the desired heat transfer rate. In order to enable this calorimeter to be operated in a power compensation mode, there is in addition a calibration heater arranged directly in the reactor. This calorimeter is suitable primarily for small sample volumes not exceeding about 50 ml.

The reaction calorimeters described above have the disadvantage that they cover only a relatively small temperature range from about −30° C. to about +150° C. and, further, that a large, voluminous and powerful electric supply is required, with the result that the control of the internal reactor temperature becomes cumbersome and slow. The limits of the temperature range are determined in particular by the initial temperature of the coolant. The temperature control devices and/or Peltier elements that are used can change the reactor temperature only by a certain amount in relation to the coolant temperature, and this amount may differ between the cooling mode and the heating mode. In addition, for example, the calorimeter described by Zogg et al. is designed only for small sample volumes.

Particularly in processes whose purpose is not limited to the controlled heating or cooling of a sample but extends to the determination of chemical and/or physical parameters, demanding requirements are imposed on the capability, the accuracy and the operative temperature range of the temperature control device. These requirements, which besides fast and efficient temperature control over a wide temperature range also include the size and compact design of the thermostat as well as cost-effectiveness and efficient use of resources, are difficult to realize particularly for larger sample volumes. For example in laboratory applications, it would be desirable to be able to use the same thermostat for the temperature control of sample volumes of a few microliters up to several hundred milliliters.

Therefore, an object of the present invention is to develop a calorimeter with an improved temperature control device, which device ensures a fast and efficient temperature regulation for sample volumes up to several hundred milliliters over a wide temperature range, and which can at the same time be made in a compact design and at a favorable cost.

This task is solved by a calorimeter with the capability to regulate an internal reactor temperature as well as by a temperature control device for a calorimeter according to the invention.

SUMMARY OF THE GENERAL INVENTIVE CONCEPT

A calorimeter according to the invention comprises at least one reactor for receiving a sample, and a reactor jacket surrounding the reactor. The calorimeter further comprises a reactor-heating device and a reactor-cooling device that regulate an internal reactor temperature. The reactor-cooling device comprises a thermoelectric cooling element that is thermally connected to a coolant. The calorimeter according to the invention is distinguished in that the reactor-cooling device and the reactor-heating device are individual units, both of which are thermally connected to the reactor by way of the reactor jacket.

The separation of reactor cooling device and reactor heating device is very advantageous because the individual components can be operated in an optimal way and a significantly broader temperature range can be covered. The temperature range of a calorimeter that is covered by a temperature control unit depends primarily on the maximum cooling power that can be generated by the thermoelectric reactor-cooling device and the maximum heating power that can be generated by the reactor-heating device.

The calorimeter may further comprise a control unit and a temperature sensor, which temperature sensor is arranged in the reactor and serves to measure an actual reactor temperature. The control unit preferably comprises at least one operating program for regulating the power of the reactor-heating device and the power of the reactor-cooling device, and further comprises at least one temperature control program having at least one reactor set temperature, so that the actual reactor temperature can be adjusted to a given reactor set temperature.

The actual heat transfer to or from the reactor and thus the heating rate of the reactor-heating device or the cooling rate of the reactor-cooling device is thus regulated by way of the current actual reactor temperature and the prescribed set reactor temperature. The different units allow a particularly fast and simple temperature regulation by means of the control unit, as the individual units do not have to be switched over from heating to cooling but are used either exclusively for heating or exclusively for cooling, an arrangement which has the additional advantage of being more energy-efficient.

The operating program can be configured for a time-optimized and/or a power-optimized adjustment of the the set reactor temperature. In choosing between a time-optimized and/or a power-optimized setting one should also consider the reaction that is to be investigated, since strongly exothermic reactions in particular must only be heated slowly and carefully so as not to accelerate the reaction too strongly.

The thermoelectric cooling element used preferably comprises at least one Peltier element that is operated with a DC voltage. The Peltier element is installed so that its hot side is always directed towards the coolant and its cold side towards the reactor, so that the Peltier element only performs the function of transferring heat from the reactor to the coolant.

This orientation of the at least one Peltier element is particularly advantageous, because in this way the operating lifespan of the Peltier element can be maximized. That is, the Peltier element is being operated in its preferred direction of heat flow, wherein the manufacturer-specified polarity of the electrical terminals is respected.

Operation with a DC voltage is advantageous primarily because Peltier elements can otherwise during operation generate a voltage of their own which, depending on the thermal situation, can have the opposite polarity of the applied current. Furthermore, Peltier elements used in accordance with the invention can be operated and controlled with electrical circuits that are much simpler and thus more cost-effective in comparison to a Peltier element that is used for both cooling and heating.

The maximum temperature difference that can be attained between the "hot" side and the "cold" side of a Peltier element, and thus the maximum temperature reduction that can be achieved with Peltier elements is limited, amounting to about 50K with the currently available single-stage thermoelectric elements. Accordingly, the "cold" side can be at most about 50K colder than the "hot" side.

This maximally attainable temperature difference results from the fact that the amount of heat being pumped as a result of the thermo-electric effect is proportional to the current flowing through the element, while the electrical losses increase in quadratic proportion with the current. At a certain level of current, the increase of the electrical power loss exceeds the increase in the rate at which the heat is being pumped, so that it becomes impossible to lower the temperature any further. On the other hand, if Peltier elements are used with reverse polarity, i.e., not in conformance with specifications, for heating and cooling, a drastic reduction of their operating lifespan and thus also an increase in maintenance costs is to be expected. The operating life is additionally shortened if the elements are used in an overload mode in order to attain a higher heating rate.

In a further embodiment of the present invention, the thermoelectric cooling element may comprise a plurality of single-stage Peltier elements or at least one multi-stage Peltier element. Multi-stage Peltier elements are, in most cases, of asymmetric configuration, because those Peltier elements that are arranged downstream in the direction of heat flow have to remove not only the heating power used for cooling, but also the accumulated electrical power loss due to dissipation in the preceding Peltier elements in the thermal chain. The Peltier elements located farther downstream in the heat flow therefore have a several times larger capacity than the Peltier elements that are more upstream in the order of sequence. For each stage, the capacity is increased by a factor of about two to five. In particular for multi-stage Peltier elements it is advantageous to operate these in the correct polarity, because in addition to the aforementioned disadvantages, the asymmetric configuration may lead to local overload or even destruction of the Peltier elements of smaller capacity.

The number of Peltier elements being used can be selected based on the desired maximum cooling power and/or the sample volume to be cooled. When several Peltier elements are used, they can be arranged in series or in parallel and can be constituted either as single-stage elements or multi-stage elements. With an individual single-stage Peltier element, the sample temperature can be lowered by about 50K and specifically to about 30K below the coolant temperature. By using multiple stages of elements, particularly in a serial arrangement, the maximum cooling range can be expanded. With each stage, a maximum temperature difference of up to about 50K can be achieved. For the same sample volume, a two-stage element can thus lower the sample temperature by a maximum of about 100K, a three-stage element by a maximum of about 150K, etc.

The operation of thermoelectric cooling element requires no more than a simple, unipolar current source which can be operated for example with a simple pulsewidth-modulated control unit.

The reactor-cooling device preferably interacts with a coolant which has an essentially constant inlet temperature or coolant temperature independent of the internal reactor temperature. This is advantageous because it offers the possibility to operate a plurality of reactor-cooling devices and thus also a plurality of calorimeters with the same coolant. In addition it becomes unnecessary to use a unit for adjusting or regulating the coolant temperature, such as a thermostat or cryostat, which is required in the calorimeters of the known prior art. As a result the temperature control device according to the invention can be given a more compact design with smaller dimensions. Furthermore, the constant coolant temperature allows a simple and precise regulation of the sample temperature. The coolant temperature can be kept essentially constant over the entire temperature range of the reaction calorimeter.

The thermoelectric cooling element functions in particular as a heat pump transferring the heat given off and/or generated by the sample to the coolant. The coolant temperature is preferably selected so that an efficient heat removal from the reactor is ensured.

At a coolant temperature of about +10° C., i.e., about the temperature of tap water, the lowest temperature that can be attained with a single-stage Peltier element is about −40° C. to −20° C. If the sample needs to be cooled only to about 0° C., it is possible to use for example ambient air with a temperature of as much as +25° C. as coolant.

How low a temperature minimum can be achieved depends directly on the cooling power of the reactor-cooling device and on the inlet temperature of the coolant. The lower the coolant temperature, the lower is the minimum of the internal reactor temperature that can be reached using the same cooling element. The minimum internal reactor temperature can be lowered further by using a coolant with a lower coolant temperature and/or a cooling element with bigger cooling power such as for example a multi-stage Peltier element.

Besides water, it is also possible to use other known liquid or gaseous fluids as coolant. Furthermore, the heat that develops can also be carried away through the evaporation of a refrigerant medium.

In one exemplary embodiment, the reactor-heating device is arranged between the reactor jacket and the reactor-cooling device, so that both units can interact with optimal effect on the reactor and/or the reaction medium arranged inside the reactor and so that, additionally, excess heat of the reactor-heating device can be carried away from the reactor.

The reactor-heating device can be configured as an electrical resistance heater, an inductive heater, or an electromagnetic heater. An electromagnetic heater can heat a sample, e.g., through electromagnetic radiation.

With the reactor-cooling device and the reactor-heating device according to the invention, the sample temperature or the internal reactor temperature can be regulated over a wide temperature range. A preferred temperature range lies between about −50° C. and about +200° C., and in particular between about −30° C. and about +180° C.

The upper temperature limit is influenced by the power of the reactor-heating device and, of course, also by the tolerance to thermal exposure of the materials that are being used. By using a suitable thermoelectric cooling element, a suitable reactor-heating device, a coolant, and/or by selecting suitable materials, a calorimeter according to the invention can therefore also be designed for other temperature ranges.

In addition, a heater element whose power can likewise be regulated with the control unit may be arranged inside the reactor. This heater element is used in particular when the calorimeter is operated in the so-called power compensation mode, and it is configured preferably as a resistance heater.

The reactor jacket may be configured essentially as a material block with a high thermal conductivity or as a double-walled reactor jacket with a cavity for the reactor. The reactor may have a volume of about 5 ml to about 1000 ml, preferably from 5 ml to about 500 ml, and more preferably, from about 20 ml to about 150 ml.

The reactor jacket configured as a material block may comprise a material of high thermal conductivity and a cavity for the reactor. Suitable materials include, among others, a variety of metals such as copper or aluminum, metal alloys or ceramics.

The double-walled reactor jacket is preferably filled with a fluid temperature-control medium. Suitable choices for a temperature-control medium comprise a multitude of liquid and/or gaseous fluids such as for example water, different heat carrier oils such as silicone oil, or inert gases such as nitrogen or helium.

The reactor can either be an insertable unit that is set into a seating recess in the reactor jacket, or it can be a recess or cavity in the reactor jacket that may be directly fed with the reaction medium. When a seating recess is provided, the seating recess should be designed to fit the insertable unit as accurately as possible in order to minimize thermal losses. The configuration as a cavity that directly receives the sample suggests itself if the reactor jacket comprises a chemically inert material, as is the case when a double-walled glass reactor is used.

Another exemplary embodiment of a calorimeter of the present invention may comprise at least two reactors whose internal reactor temperatures can be regulated independently of each other by means of a common control unit, wherein each reactor comprises a reactor-heating device and a reactor-cooling device, and all reactor-cooling devices are preferably in thermal connection with the same coolant. With such an arrangement the reactors can be operated in parallel, which is advantageous in particular for serial investigations.

A further aspect of the invention concerns a temperature control device for a thermoanalytical instrument, in particular for a calorimeter or a reaction calorimeter. The temperature control device comprises a reactor-heating device, reactor-cooling device and a control unit, wherein the reactor-cooling device comprises at least one thermoelectric cooling element which is thermally connected to a coolant. The temperature control device is characterized by the fact that the reactor-cooling device and the reactor-heating device are individual units and that the coolant has an essentially constant inlet temperature that is independent of the internal reactor temperature.

A temperature control device according to the invention can on the one hand be used as an instrument by itself for controlling the temperature of small as well as larger sample volumes, and on the other hand, also in combination with a calorimeter.

A temperature control device according to the invention can also be used to control the temperature of several calorimeters that are arranged with their individual reactor-heating devices and thermoelectric cooling elements in a common housing and/or in separate housings. The internal reactor temperature of each calorimeter can be regulated independently without having to adjust the coolant temperature. In this arrangement the coolant temperature is likewise essentially constant. The temperature control device can have a common coolant circuit and/or separate coolant circuits for the individual calorimeters.

A temperature control device according to the present invention may be particularly well-suited to applications where the temperature control device interacts with a thermoanalytical device for the determination of thermogravimetric, calorimetric, thermodynamic, rheological or thermomechanical properties of a sample. For these applications it is desirable to use a fast and precise temperature regulation as well as an efficient and compact temperature control device.

A temperature control device according to the present invention is preferably configured so that heat always flows from the "cold" to the "hot" side of the thermoelectric cooling element. Since the thermoelectric cooling element (preferably at least one Peltier element) is always operated with the specified polarity, the direction of the heat flow through the cooling element is essentially independent of the temperatures acting on the cooling element from the outside, which comprise among others the sample temperature and the coolant temperature.

The maximum value of the sample temperature that can be attained with a temperature control device is determined primarily by the materials of the temperature control device and by the unit in which the sample is arranged. When the sample is being heated, the cooling element simply transfers excess heat to the coolant, so that a local overheating of the element(s) is avoided. The cooling element can in this case be active or passive. Using Peltier elements in a passive mode corresponds to a thermoelectric current generation, which has no influence on the operating lifespan of the Peltier elements.

Arrangements where a temperature control device according to the invention is used in combination with a calorimeter are very desirable because, in comparison to calorimeters of the known state of the art, the size of the instrument as a whole can be reduced and the temperature control device can be operated with a more efficient use of energy, whereby a more cost-effective production of the device is made possible.

BRIEF DESCRIPTION OF THE DRAWINGS

An exemplary calorimeter according to the invention having a reactor-cooling device, a reactor-heating device, and a temperature control device, are described below. These and other features and aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
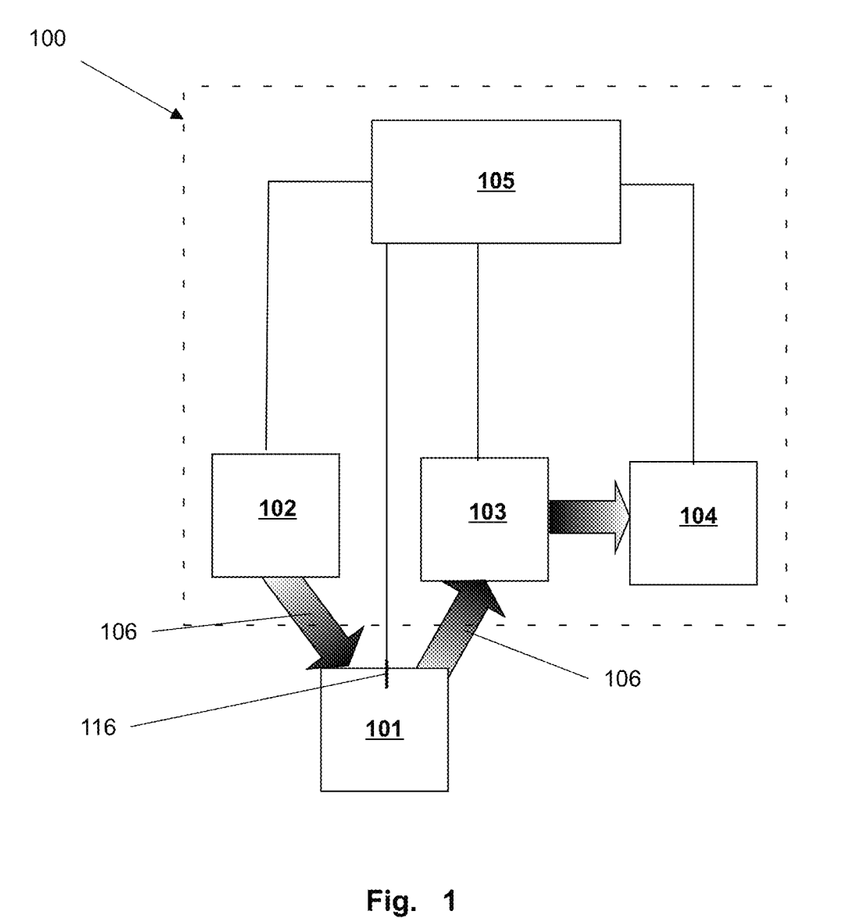
FIG. 1 is a greatly simplified schematic representation of the operation and structural concept of an exemplary temperature control device according to the present invention.

FIG. 1 shows, in a greatly simplified schematic view, the basic structure and functional concept of an exemplary temperature control device 100 of the present invention. As shown, a sample 101 may be arranged in a reactor and thermally connected to the temperature control device 100, which contains a reactor-heating device 102, a reactor-cooling device with a thermoelectric cooling element 103, and a coolant 104 that is thermally connected to the thermoelectric cooling element 103. The regulation and/or control of the temperature control device 100 takes place by way of a control and/or regulation unit 105 which also supplies the electric current required for the operation of the individual elements. The control and/or regulation unit 105 is further connected to at least one temperature sensor 116 that serves to measure the sample temperature, i.e., the actual temperature inside the reactor.

The heat flow between the thermostat 100 and sample 101 is symbolized here by arrows 106. In a case where the sample 101 is heated by the heating element 102, the excess heat can be pumped by the thermoelectric cooling element 103 into the coolant 104. Depending on the amount of heat to be transferred, the cooling element 103 can conduct the excess heat to the coolant 104 in an active or passive mode of operation. If the sample is to be cooled, the delivery of heat from the reactor-heating element 102 to the sample 101 is reduced or switched off and the reactor-cooling device 103 is activated, so that heat is now being actively removed from the sample 101 and transferred by the cooling element 103 to the coolant 104.

In this way the temperature control device 100 can deliver heat to, and/or remove heat from, the sample 101 that is arranged in the reactor and thereby regulate the temperature of the sample 101 or the internal reactor temperature within its temperature range, which can be influenced through the selection of the individual components. When the sample is being heated as well as when it is being cooled, the coolant 104 has an essentially constant inlet temperature and/or coolant temperature. The attribute "essentially constant" means here that the temperature is constant within the limits of the measurement uncertainty and within the specifications of the instrument.

Figure 2:
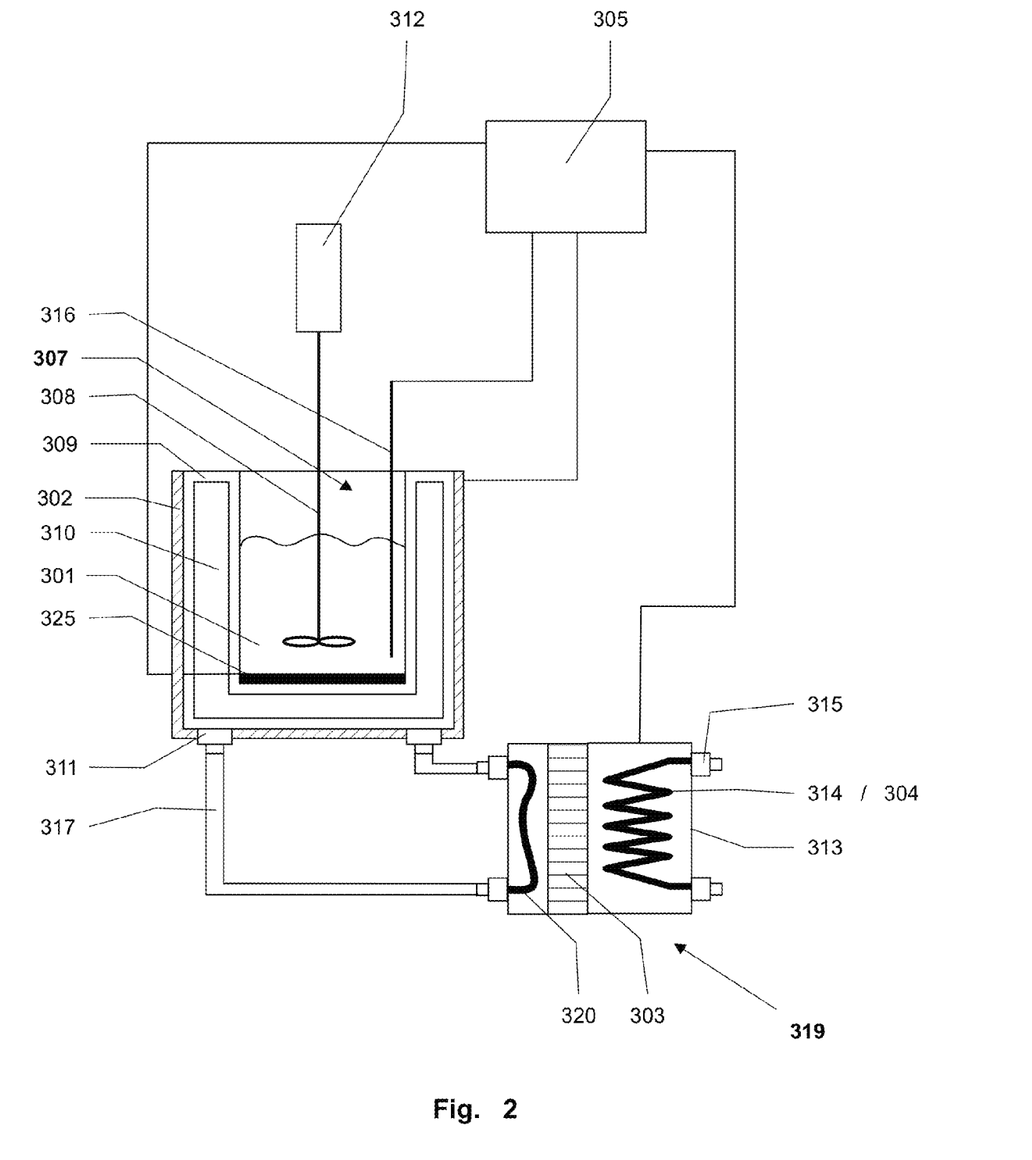
FIG. 2 is a schematic representation of an exemplary calorimeter according to the present invention, the calorimeter having a fluid-filled reactor jacket.
Figure 3:
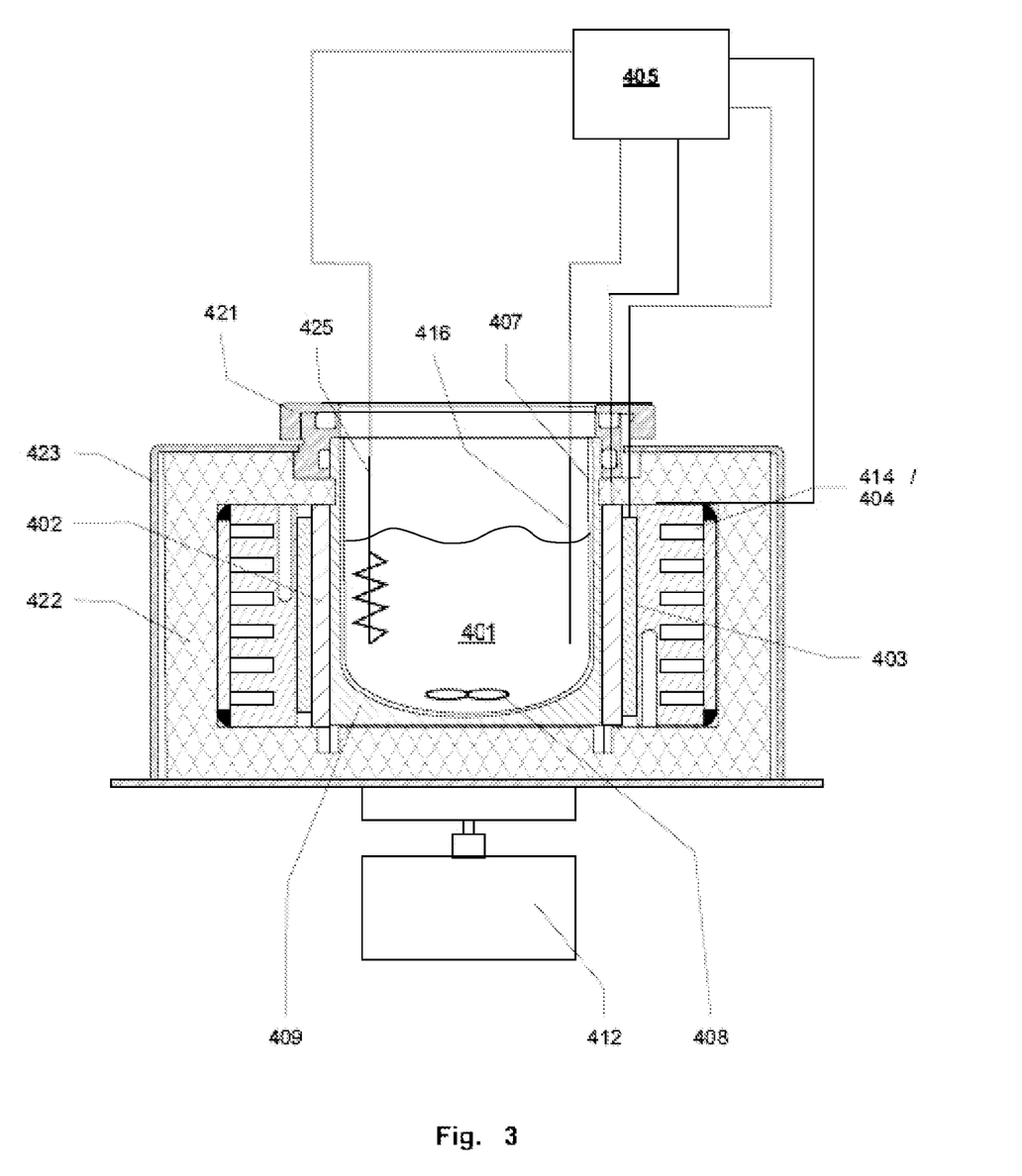
FIG. 3 is a sectional view of another exemplary calorimeter according to the present invention, the calorimeter having a metal block as reactor jacket.
Figure 4:
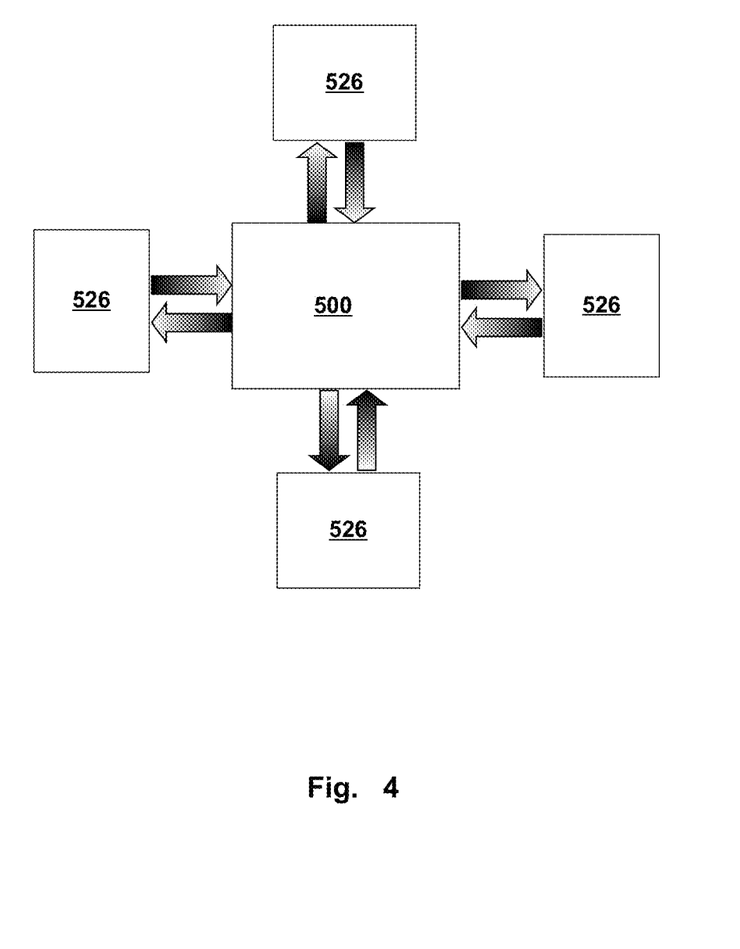
FIG. 4 schematically illustrates an arrangement of several exemplary calorimeters according to the present invention, the individual internal reactor temperatures of which are regulated by a common control unit.

Different calorimeters and, more specifically, reaction calorimeters according to the present invention whose internal reactor temperature can be regulated with a temperature control device, are shown in FIGS. 2 to 4.

The calorimeter shown in FIG. 2 comprises a reactor 307 for receiving a sample 301. Arranged in the reactor 307 is a stirrer 308 that is connected to a motor 312 and serves to mix up the sample 301. Also arranged in the reactor 307 is a heating element 325 that can act directly on the sample when the reaction calorimeter is operated in a power compensation mode. The reactor 307 is surrounded by a double-walled reactor jacket 309 filled with a temperature-control medium 310 that is circulated through a cooling device 319. The cooling device 319 is connected through suitable conduits 317 to the reactor jacket 309. The reactor 307 is configured as a cavity inside the reactor jacket 309, so that the reactor jacket 309 and the reactor 307 together represent a unit.

The cooling device 319 has two separate circuits 314, 320, one for the temperature-control medium 310 and one for the coolant 304. Both of the circuits 314, 320 are thermally connected to a thermoelectric cooling element 303 that comprises at least one multi-stage Peltier element whose "hot" side is thermally connected to the coolant 304 and whose "cold" side is thermally connected to the temperature-control medium 310. The coolant circuit 314 can be supplied through the connector ports 315 with a suitable coolant 304. The reactor-cooling device in this embodiment comprises the temperature-control medium 310, the coolant 304, the cooling device 319 and the thermoelectric cooling element 303.

Besides the cooling device 319 the calorimeter shown in FIG. 2 further comprises a reactor-heating device 302 surrounding the reactor jacket 309 and a control and/or regulation unit 305 that is connected to the reactor-heating device, to at least one temperature sensor 316 for detecting the internal reactor temperature, and to the cooling device 319. The reactor-heating device 302 is, in this case, configured as an inductive heating device.

The heating element 325 that is arranged in the reactor 307 is, in this case, configured in the form of a heating coil at the floor of the reactor 307. As an alternative, it is also possible to use a heating rod that is arranged in the reactor.

FIG. 3 gives a sectional view of a further calorimeter according to the invention. The calorimeter comprises a reactor 407 for receiving a sample, which can be closed off with a reactor lid 421. Arranged inside the reactor 407 are a stirrer 408 which interacts with a stirrer motor 412, a heating element 425 in the form of an electrical resistance heater for the operating mode of power compensation, and a temperature sensor 416 for the measurement of the sample temperature and/or the actual temperature in the reactor 407. The calorimeter as well as a reactor-heating device and the reactor-cooling device are controlled by a control and/or regulation unit 405.

The reactor 407 is surrounded by a reactor jacket 409 which is configured here as a material block with a high thermal conductivity and with a cavity into which the reactor 407 can be set. Preferred materials for the reactor jacket 409 include aluminum or copper, but other metals, metal alloys or ceramics could also be used. The walls of the reactor jacket 409 are surrounded by a reactor-heating device 402, which is configured as an electrical resistance heater arranged between the reactor jacket 409 and the reactor-cooling device 403. The reactor-cooling device 403 in this embodiment comprises at least one single-stage Peltier element.

The reactor-heating device 402 is arranged between the reactor-cooling device 403 and the reactor 407, so that heat can on the one hand be given off to the reactor 407 and excess heat can on the other hand be removed from the reactor 407, or the reactor 407 can be cooled, by the reactor-cooling device 403.

The thermal contact surfaces between the reactor jacket 409 and the reactor-heating device 402 as well as between the reactor-heating device 402 and the cooling element 403 should be as large as possible in order to allow a rapid heat exchange. At the same time, with this arrangement of reactor jacket 409, reactor-heating device 402, and cooling element 403, the heat that may be generated during operation in the cooling element 403, particularly in the cooling element, can be removed directly through the coolant 404 without affecting a sample that is arranged in the reactor 407.

The cooling element 403, in turn, is surrounded by conduits 414 that are filled with a coolant 404. Different fluids can be used as coolant 404, which coolant can be introduced through connector ports (not shown in the drawing) into the conduits 414, removed from the latter, or pumped through the conduits by suitable means. The choice of the coolant 404 and its inlet temperature or coolant temperature depends primarily on the desired cooling power. A currently available single-stage Peltier element can produce a temperature reduction of about 30K to 50K in relation to the temperature of the coolant 404. To increase the cooling power of the reactor-cooling device, one can use several single-stage Peltier elements or at least one multi-stage Peltier element. The cooling element 403 is thermally connected to the coolant 404 and can pump or conduct heat from the sample 401 to the coolant 404. For sample temperatures significantly above the coolant temperature, the Peltier elements of the cooling element 403 are inactive and simply pass the heat on to the coolant 404 by passive heat conduction. For applications in the laboratory one could for example use water as the coolant 404.

The Peltier elements 403 of the reactor-cooling device are arranged so that their "hot" side faces towards the coolant 404 and their "cold" side faces towards the reactor-heating device 402. As a result, the heat flow through the cooling element 403 always has the same direction, and it is possible to hold the temperature of the coolant essentially constant during operation over the entire temperature range of the temperature control device, as the coolant 404 is used exclusively for the removal of the heat.

The internal reactor temperature is regulated by way of a control- and/or regulation device 405 that increases or decreases the actual or currently existing temperature in the interior of the reactor, as measured for example with a temperature sensor 416, to a prescribed set temperature. This is accomplished by either delivering heat to the reactor 407 with the reactor-heating device 402 or by removing heat with the cooling element 403. Of course, it is also possible to subject the reactor 407 as well as a sample arranged inside the reactor to a prescribed temperature profile.

In calorimetric measurements it is of practical advantage if the sample is examined in a thermally closed-off or at least enclosed environment. For this reason, the calorimeter and the thermostat are located in a housing 423 which is lined with insulating material 422. In this way, it is possible to identify the different heat flow currents and derive chemical and/or physical parameters from the investigations. For the measurement of the heat flow currents one can use for example heat flow sensors and/or temperature sensors which detect at least the heat exchange of the sample with the reactor and/or the reactor jacket. In addition, the temperatures and/or heat flow currents in further components of the calorimeter and/or the temperature control device should also be measured. Since calorimeters, including their general structure and operating principle, are basically known, the different possibilities for arranging such sensors are not explicitly shown herein.

FIG. 4 schematically represents an arrangement of several calorimeters 526—four in the illustrated example—which are thermally connected to a common temperature control device 500. The temperature control device 500 functions essentially in the same way as the temperature control device shown in FIG. 1. The calorimeters 526 are preferably identical in their design, so that they may be operated in parallel, for example to perform serial experiments on similar samples or reaction mixtures.

LIST OF REFERENCE SYMBOLS USED HEREIN 100, 500 temperature control device
101, 301 sample
102, 302, 402 reactor-heating device
103, 303, 403 thermoelectric cooling element
104, 304, 404 coolant
105, 305, 405 control- and/or regulation unit
106 heat flow
307, 407 reactor
308, 408 stirrer
309, 409 reactor jacket
310 temperature-control medium
311 connector
312, 412 stirrer motor
313 cooler
314, 414 conduit pipe, circuit
315 connector, connector port
116, 316, 416 temperature sensor
317 conduit pipe
319 cooling device
320 circuit
421 reactor lid
422 insulation
423 housing
325, 425 calibration heater, heating element
526 calorimeter While certain embodiments of the present invention are described in detail above, the scope of the invention is not to be considered limited by such disclosure, and modifications are possible without departing from the spirit of the invention as evidenced by the following claims:

What is claimed is:
1. A calorimeter comprising:
a reactor for receiving a sample, a reactor jacket surrounding the reactor; and
a temperature control device for regulating an internal temperature within the reactor, the temperature control device comprising:
an individual reactor-heating device for providing an amount of heat, the reactor-heating device being thermally connected to the reactor by way of the reactor jacket,
an individual reactor-cooling device for removing an amount of heat, the reactor-cooling device being separated from the reactor-heating device and is thermally connected to the reactor by way of the reactor jacket, the reactor-cooling device being a thermoelectric cooling element that is also thermally connected to a coolant having a substantially constant inlet temperature independent of the internal reactor temperature;
a temperature sensor, the temperature sensor arranged in the reactor and adapted to measure an actual reactor temperature; and
a control unit having at least one operating program and at least one temperature control program,
wherein the at least one temperature control program is designed for adjusting the actual reactor temperature to a given reactor set temperature, and wherein the at least one operating program is for regulating the heat provided by the reactor-heating device and the heat removed by the reactor-cooling device, while permitting electrical current to be provided, at any given time, to no more than one of the reactor-heating device and the reactor-cooling device, and wherein the at least one operating program is designed for one or both of a time-optimized adjustment of the reactor set temperature and a power-optimized adjustment of the reactor set temperature.

2. The calorimeter of claim 1, further comprising a heating element arranged in the reactor, the amount of heat provided by the heating element regulated by the control unit.

3. The calorimeter of claim 1, wherein:
the thermoelectric cooling element comprises at least one Peltier element.

4. The calorimeter of claim 1, wherein the thermoelectric cooling element is an individual single-stage Peltier element.

5. The calorimeter of claim 1, further comprising a cooler for the coolant, the cooler cooperating with the reactor-cooling device and having an essentially constant inlet temperature independent of the internal temperature of the reactor.

6. The calorimeter of claim 1, wherein the reactor-heating device is arranged between the reactor jacket and the reactor-cooling device.

7. The calorimeter of claim 1, wherein the reactor jacket is comprised of a material block having a high thermal conductivity.

8. The calorimeter of claim 1, wherein the reactor jacket is a double-walled reactor jacket having a cavity for the reactor, and is filled with a temperature-control medium.

9. The calorimeter of claim 1, wherein at least two reactors are present, and wherein the internal temperatures of the at least two reactors can be regulated independently of each other by means of a shared temperature control device control unit.

10. A method for performing reaction calorimetry, comprising:
(a) providing a calorimeter, the calorimeter comprising:
a reactor for receiving a sample, a reactor jacket surrounding the reactor, and
a temperature control device for regulating an internal temperature within the reactor, the temperature control device having a control unit with at least one operating program and at least one temperature control program, a temperature sensor arranged in the reactor for measuring an actual temperature of the reactor, an individual reactor-heating device that is thermally connected to the reactor by way of the reactor jacket, and an individual reactor-cooling device that is separated from the reactor-heating device and is thermally connected to the reactor by way of the reactor jacket, the reactor cooling device being a thermoelectric cooling element that is also thermally connected to a coolant having a substantially constant inlet temperature independent of the internal reactor temperature;
(b) initiating a chemical reaction within the reactor;
(c) running the at least one temperature control program to adjust the actual temperature of the reactor to a given reactor set temperature; and
(d) running the at least one operating program to regulate an amount of heat provided by the reactor-heating device and an amount of heat removed by the reactor-cooling device, while permitting electrical current to be provided, at any given time, to no more than one of the reactor-heating device and the reactor-cooling device, wherein the at least one operating program is designed for one or both of a time-optimized adjustment of the reactor set temperature and a power-optimized adjustment of the reactor set temperature.

11. The method of claim 10, wherein at least two reactors are present, and wherein the internal temperatures of the at least two reactors are regulated independently of each other by means of a shared control unit.

* * * * *